United States Patent
Edelmann

(10) Patent No.: US 7,591,981 B2
(45) Date of Patent: Sep. 22, 2009

(54) APPARATUS AND METHOD FOR CRYOSUBSTITUTION AND EMBEDDING OF BIOLOGICAL SPECIMENS

(75) Inventor: Ludwig Edelmann, Homburg/Saar (DE)

(73) Assignee: Leica Mikrosysteme GmbH, Vienna (AT)

( * ) Notice: Subject to any disclaimer, the term of this patent is extended or adjusted under 35 U.S.C. 154(b) by 486 days.

(21) Appl. No.: 11/212,351

(22) Filed: Aug. 26, 2005

(65) Prior Publication Data

US 2006/0045813 A1    Mar. 2, 2006

(30) Foreign Application Priority Data

Aug. 31, 2004   (DE) ................. 10 2004 041 965

(51) Int. Cl.
*B01L 3/00*         (2006.01)
(52) U.S. Cl. ................................... 422/102
(58) Field of Classification Search ............. 422/102
See application file for complete search history.

(56) References Cited

U.S. PATENT DOCUMENTS

| 6,516,620 B2 | 2/2003 | Lang ............... 62/64 |
| 6,536,219 B2 | 3/2003 | Peters ............. 62/62 |
| 6,537,826 B1 | 3/2003 | Horigane ........ 436/176 |
| 2003/0014879 A1* | 1/2003 | Horigane ........ 34/284 |

FOREIGN PATENT DOCUMENTS

| DE | 2739796 | 3/1979 |
| DE | 2944464 | 5/1981 |
| DE | 3425744 | 1/1986 |
| DE | 9104344 U | 8/1991 |
| DE | 19842797 | 1/2000 |
| DE | 19852835 | 5/2000 |
| DE | 10065143 | 6/2002 |
| EP | 0611445 | 8/1994 |
| EP | 0637741 | 2/1995 |
| EP | 0853238 | 7/1998 |
| JP | 2004198347 A | 7/2004 |
| WO | WO 03/050509 A1 | 6/2003 |

OTHER PUBLICATIONS

Leica EM AFS Recipe Book.
Leica EM PACT High Pressure Freezer.

* cited by examiner

*Primary Examiner*—Walter D Griffin
*Assistant Examiner*—Bobby Ramdhanie
(74) *Attorney, Agent, or Firm*—Simpson & Simpson, PLLC

(57) ABSTRACT

An apparatus and a method for cryosubstitution and embedding of biological specimens is disclosed. The apparatus encompasses a container (6) for receiving at least one specimen carrier (2) having a specimen (4). The specimen carriers (2) are placed into troughs (12) of the container (6). Configured in each trough is a step (20) by which the specimen carrier (2), together with the specimen (4), is held in the container (6).

25 Claims, 4 Drawing Sheets

APPARATUS AND METHOD FOR CRYOSUBSTITUTION AND EMBEDDING OF BIOLOGICAL SPECIMENS

CROSS REFERENCE TO RELATED APPLICATIONS

This application claims priority of the German patent application 10 2004 041 965.5. which is incorporated by reference herein.

FIELD OF THE INVENTION

The invention concerns an apparatus for cryosubstitution and embedding of biological specimens. The invention concerns in particular an apparatus for cryosubstitution and embedding of biological specimens that encompasses a container for receiving at least one specimen carrier having a specimen.

The invention further concerns a method for cryosubstitution and embedding of biological specimens.

BACKGROUND OF THE INVENTION

The Leica EM AFS discloses a device according to the existing art. A Dewar vessel is filled with liquid nitrogen, the Dewar neck having a chamber that is cooled to a specific temperature. The desired temperature is set via a control circuit and built-in heating elements. The substitution process usually begins at approximately −90° C. The frozen specimen is transferred into the chamber, for which purpose several different containers can be provided with which the specimens are immersed into a substitution medium, usually acetone or methanol. At this low temperature the slow process of substitution begins, in which the frozen water in the specimen is replaced by the solvent without the occurrence of recrystallization. During this process the temperature is then slowly raised, and the medium is exchanged and ultimately replaced with a low-temperature embedding medium. A UV lamp is placed onto the chamber for polymerization of the low-temperature embedding medium. The various containers for cryosubstitution and embedding are disclosed in the catalog for the Leica EM AFS. All the containers disclosed therein have the disadvantage that a loss of specimens can occur during the process of cryosubstitution and/or embedding.

There are a variety of methods and devices for effective freezing of specimens. The high-pressure freezing method yields the best results at present. After initial freezing, the frozen specimens are located in specimen carriers. These specimen carriers are illustrated on page 6 of the Leica EM PACT catalog. Detaching the small specimens (usually 0.2 mm thick and 1.2 mm in diameter) from the mount, manipulating these specimens in the substitution medium, and transferring them into an embedding mold are critical steps that often result in loss of a sample.

U.S. Pat. No. 6,516,620 discloses an apparatus for high-pressure freezing of specimens. Here the specimen carrier is clamped in on all sides into a holder, and is impinged upon by the corresponding pressure from one side. A cooling medium is sprayed from the outside onto all sides of the specimen holder in order to achieve the requisite low temperature.

U.S. Pat. No. 6,536,219 discloses an apparatus and a method for precise cryosubstitution of tissue samples. The apparatus possesses multiple depressions of different sizes and shapes for embedding. With this apparatus as well, however, the possibility that a loss of specimens may occur cannot be ruled out.

SUMMARY OF THE INVENTION

It is therefore the object of the present invention to make available an apparatus for cryosubstitution and embedding of biological specimens with which any possible specimen loss, both during transfer of the specimen into the apparatus for embedding and during the process of cryosubstitution and embedding, is considerably reduced if not entirely ruled out.

The aforesaid object is achieved by an apparatus for cryosubstitution and embedding of biological specimens comprising: a container for receiving at least one specimen carrier holding the specimen, wherein the container possesses the shape of a cylinder having a base and a sidewall and an opening opposite to the base, a plurality of troughs are embodied in the container, each for receiving one specimen carrier; wherein each of the troughs is configured with a tapering end and the tapered end of the troughs being arranged opposite the sidewall of the open cylinder, a step against which the specimen carriers rest being configured at the tapered end of each trough; and a supply conduit is provided with each of the troughs, so that a connection exists among the troughs.

A further object of the invention is to create a method for cryosubstitution and embedding of specimens with which specimen loss is almost ruled out.

The object is achieved by a method for cryosubstitution and embedding of biological specimens, comprising the following steps:

placing at least one specimen carrier, carrying a specimen, into a container that encompasses multiple troughs each for receiving one specimen carrier;

placing the specimen carrier against a step that is shaped into each of the troughs at a tapering end of the troughs;

delivering and extracting at least one medium for cryosubstitution and embedding through an introduction and extraction opening; and that each of the troughs is equipped with a supply conduit so that a connection of the troughs to the introduction and extraction opening exists;

polymerizing an embedding medium delivered to the troughs; and ejecting each shape present in the troughs, the polymerized shape carrying the specimen.

The invention has the advantage that the apparatus for cryosubstitution and embedding of biological specimens encompasses a container for receiving at least one specimen carrier having a specimen. Multiple troughs are embodied in the container, each for receiving one specimen carrier. Each of the troughs is equipped with a supply conduit, so that a connection exists among the troughs.

The supply conduit and the connection among the troughs make possible an exchange of the various media that are required for cryosubstitution and embedding. The container encompasses an introduction and extraction opening for the medium. The introduction and extraction opening is connected to the supply conduits, so that the individual troughs can be furnished, through the supply conduits, with the medium that is currently required or being used.

It is particularly advantageous if the container possesses the shape of a cylinder open at one end. The container comprises a base and a sidewall. Opposite the base, the cylinder is open or possesses there the aforementioned opening. The at least one trough, and the introduction and extraction opening, are configured in the interior of the cylinder.

The introduction and extraction opening is arranged centrally. The multiple troughs are arranged radially around the introduction and extraction opening. Each of the troughs possesses a tapering end. The tapered end of the troughs is arranged opposite the sidewall of the open cylinder.

It is particularly advantageous if the troughs are configured in a separate trough plate. The trough plate is then insertable into the container, which has the conformation of a cylinder open at the top. The trough plate is embodied, at the tapered end of each trough, with a step against which the specimen carriers rest.

The method for cryosubstitution and embedding of biological specimens is embodied in particularly advantageous fashion in that at least one specimen carrier carrying a specimen is placed into a container that encompasses multiple troughs, each for receiving one specimen carrier. Once the specimen carriers have been placed into the respective troughs, cryosubstitution and embedding are accomplished by delivering appropriate media through the introduction and extraction opening. Each of the troughs is equipped with a supply conduit, so that a connection of the troughs to the introduction and extraction opening exists. Once cryosubstitution is complete, polymerization of an embedding medium delivered to the troughs occurs. After polymerization, ejection of each of the shapes present in the troughs occurs. The polymerized shape carries the specimen.

The specimen is arranged on an elevation of the polymerized shape. The specimen carrier falls away upon ejection of the polymerized shape from the trough. This is particularly advantageous because an automatic separation of the specimen from the specimen carrier occurs after polymerization. In addition, the step shaped into the trough plate ensures immobilization of the specimen carrier during cryosubstitution and embedding, so that after polymerization of the shape, a defined location of the specimen is stipulated.

BRIEF DESCRIPTION OF THE DRAWINGS

Further advantages and advantageous embodiments of the invention may be inferred from the dependent claims and are the subject matter of the Figures that follow and their descriptions, in which specifically:

DETAILED DESCRIPTION OF THE INVENTION

Figure 1:
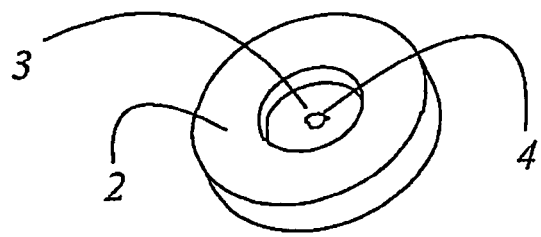
FIG. 1 is a perspective view of the specimen carrier for cryosubstitution and embedding.

FIG. 1 is a perspective view of a specimen carrier 2 that carries a specimen 4. Specimen carrier 2 is annular in configuration, and carries specimen 4 in a depression 3. Specimen 4 possesses a diameter of approximately 1.2 mm and a thickness of approximately 0.2 mm.

Figure 2:
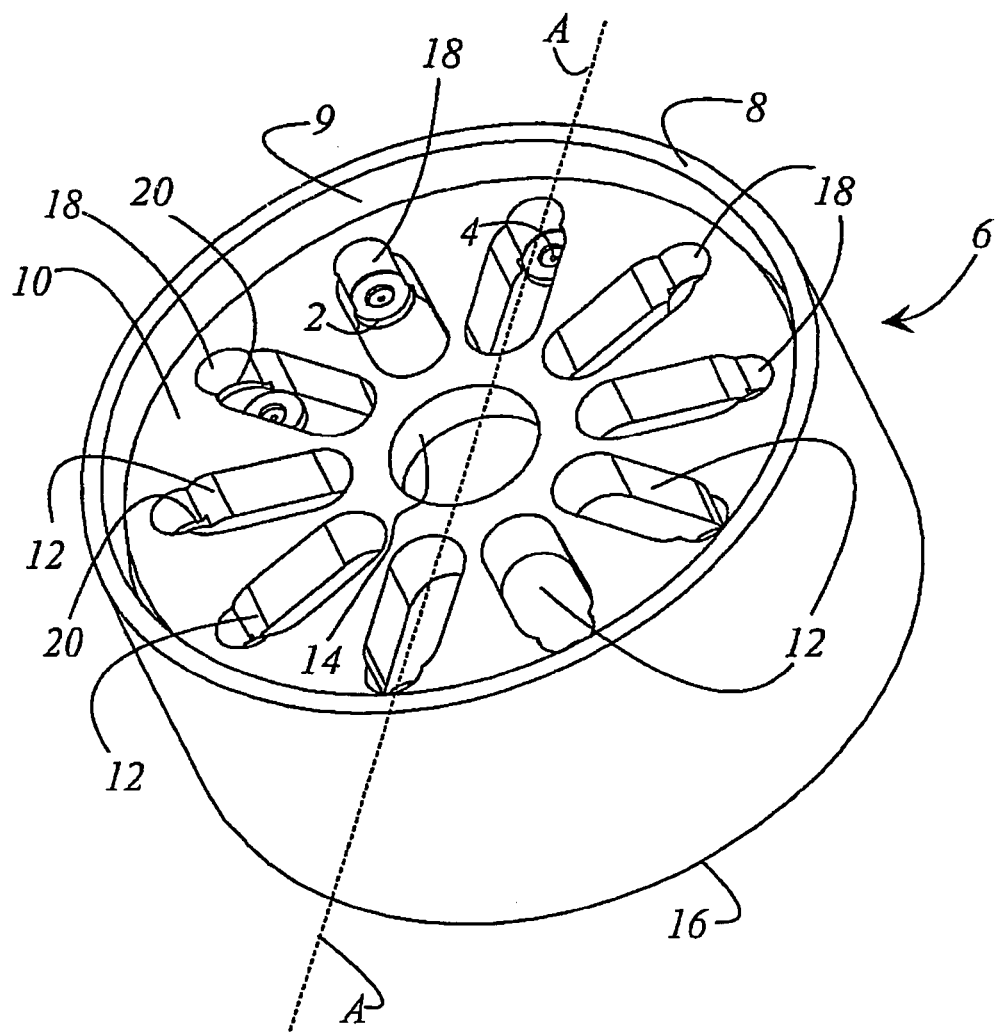
FIG. 2 is a perspective view of the container for cryosubstitution and embedding, several specimen carriers being inserted into the container.

FIG. 2 is a perspective view of a container 6 for cryosubstitution and embedding. Container 6 is cylindrical in shape and possesses a sidewall 8 and a base 16. The container is open at the end opposite base 16. Multiple troughs 12 are configured in the interior of container 6. It is particularly advantageous if troughs 12 are configured in a trough plate 10 that is removable from the inner region of container 6. In the embodiment depicted here, trough plate 10 possesses a central introduction and extraction opening 14 through which the chemicals or media necessary for cryosubstitution and embedding can be delivered and extracted. In this embodiment, troughs 12 are arranged radially around introduction/extraction opening 14. Toward side wall 8 of container 6, troughs 12 possess a tapered end 18. Tapered end 18 is configured with a step 20 with which the specimen carrier is held in the trough. One specimen carrier 4 is placed into each trough 12, and slid onto the tapering end 18 until it comes into contact against step 20.

Figure 3:
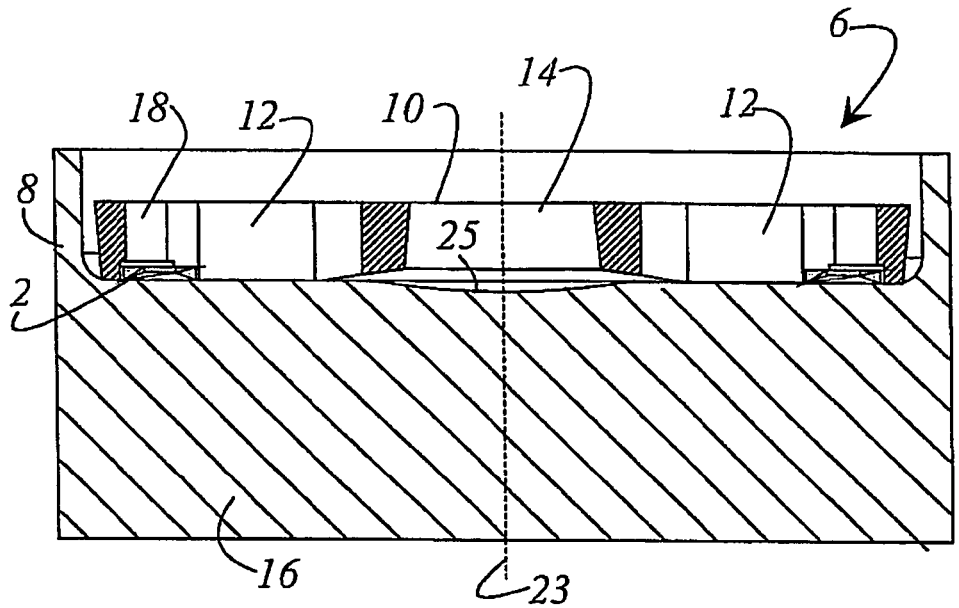
FIG. 3 is a cross section through the container along line A-A depicted in FIG. 2.

FIG. 3 is a cross section through container 6 along line A-A drawn in FIG. 2. Container 6 is embodied rotationally symmetrically about an axis 23. Introduction/extraction opening 14 is arranged about axis 23. Below introduction/extraction opening 14, base 16 of container 6 possesses a depression 25. In addition, trough plate 10 does not extend all the way to base 16 of container 6 in the region of introduction/extraction opening 14, so that as a result of the coaction between depression 25 and trough plate 10, which does not extend all the way to the base of container 6, a supply conduit to the individual troughs 12 is formed. The supply conduit is shown as item 22 in FIG. 4.

Figure 4:
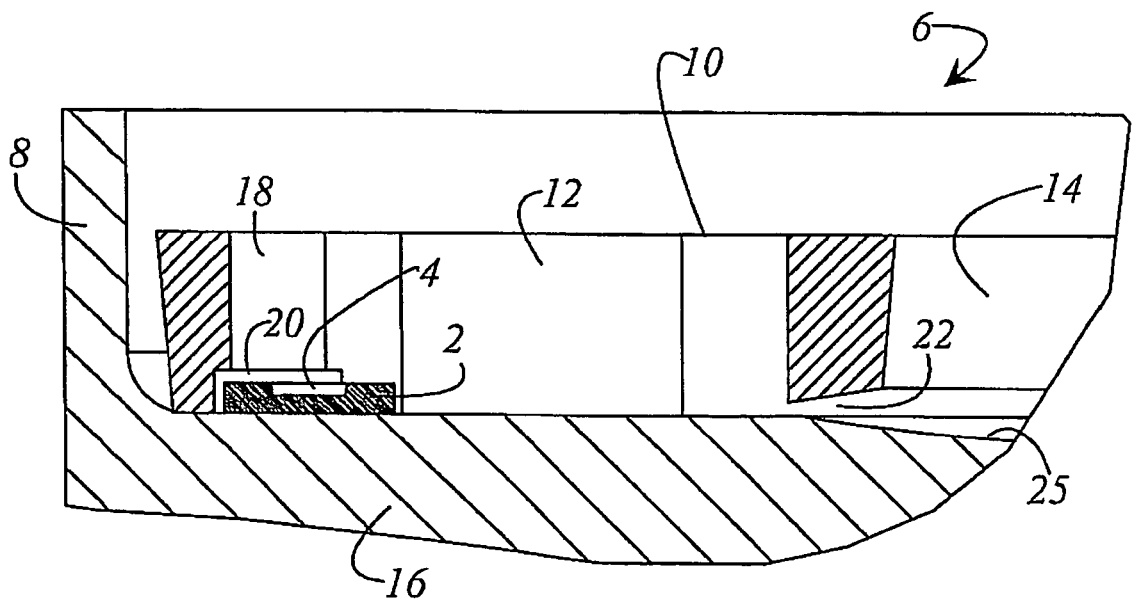
FIG. 4 is a detail view of the container for cryosubstitution and embedding, showing the location of the sample carrier in the container.

FIG. 4 is an enlarged view of container 6 in order to elucidate the retention of specimen carrier 2 in trough 12. As already mentioned in the description of FIG. 3, trough plate 10 does not extend all the way to base 16 of container 6 in the region of introduction/extraction opening 14. A supply conduit 22 from introduction/extraction opening 14 to trough 12 is thereby formed. Toward sidewall 8 of container 6, the trough terminates in a tapering end 18. Configured in the region of tapering end 18 is step 20 that partially radially wraps around specimen carrier 2.

Figure 5:
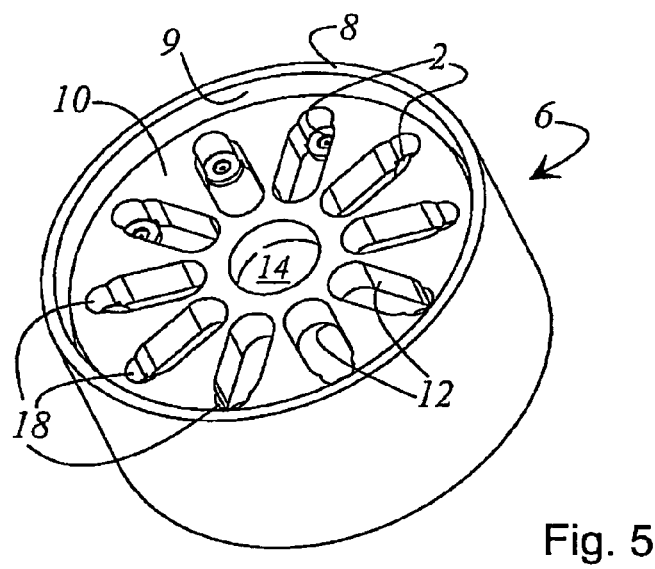
FIG. 5 is a perspective depiction of the container for cryosubstitution.

FIG. 5 is a perspective view of container 6 into whose opening 9 trough plate 10 is inserted. Several specimen carriers 2 are inserted into troughs 12.

Figure 6:
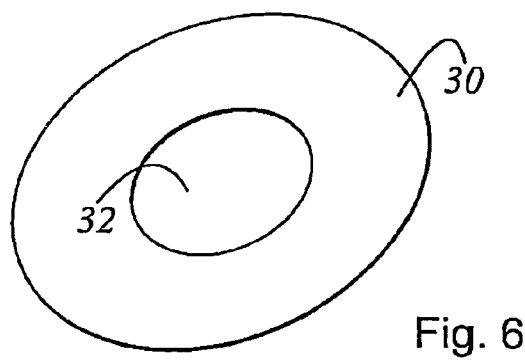
FIG. 6 shows a UV-transparent annular disk that is placed into the container for cryosubstitution and embedding prior to polymerization of the embedding medium.

FIG. 6 shows a UV-transparent annular film 30 that can be placed onto trough plate 10. Annular film 30 possesses a central opening 32 which possesses a larger diameter than introduction/extraction opening 14. Opening 32 of annular film 30 is dimensioned in such a way that in addition to access to introduction/extraction opening 14, access is also maintained to each trough 12 in trough plate 10. UV-transparent film 30 is put in place in a final step, i.e. prior to polymerization. A UV lamp (not depicted) is placed onto container 6 in order to begin polymerization of the embedding medium. If film 30 were not placed onto trough plate 10, the embedding medium would polymerize more slowly and more unevenly. Because the embedding medium contracts upon polymerization, access to each trough 12 is still necessary.

Figure 7:
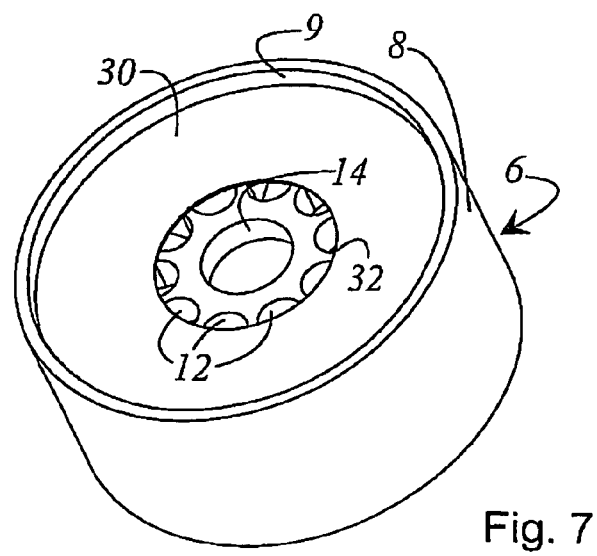
FIG. 7 is a perspective depiction of the container for cryosubstitution and embedding, the UV-transparent annular disk being placed into the container.

FIG. 7 is a perspective depiction of container 6 with UV-transparent annular film 30 in place. Opening 32 of annular film 30 permits access to introduction/extraction opening 14, and partial access to each of troughs 12.

Figure 8:
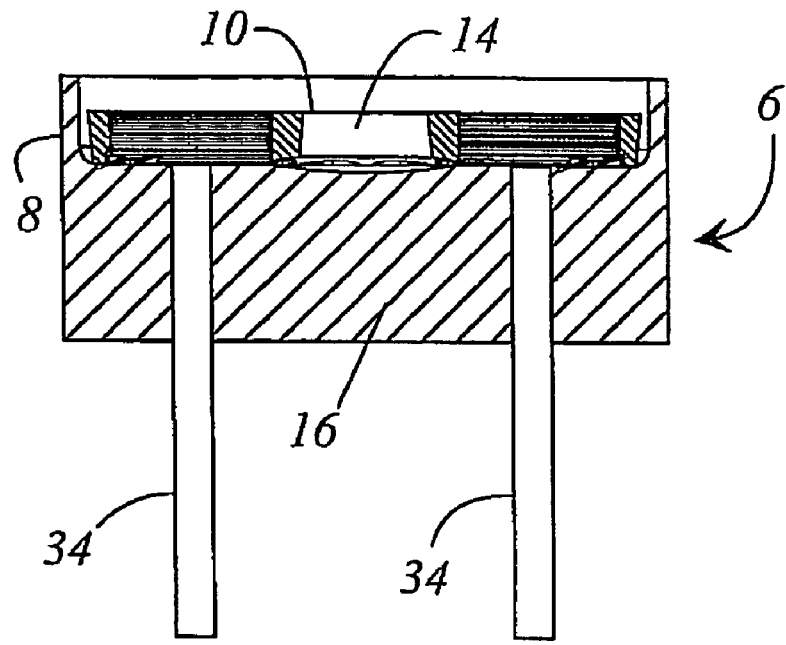
FIG. 8 schematically depicts an ejecting means with which the polymerized parts in the troughs are ejected from the container.

FIG. 8 shows an ejection means 34 that serves to eject the fully polymerized shapes in trough 12. The ejection means engages through base 16 of container 6 and acts directly on the fully polymerized embedding-medium shapes present in the individual troughs 12.

Figure 9:
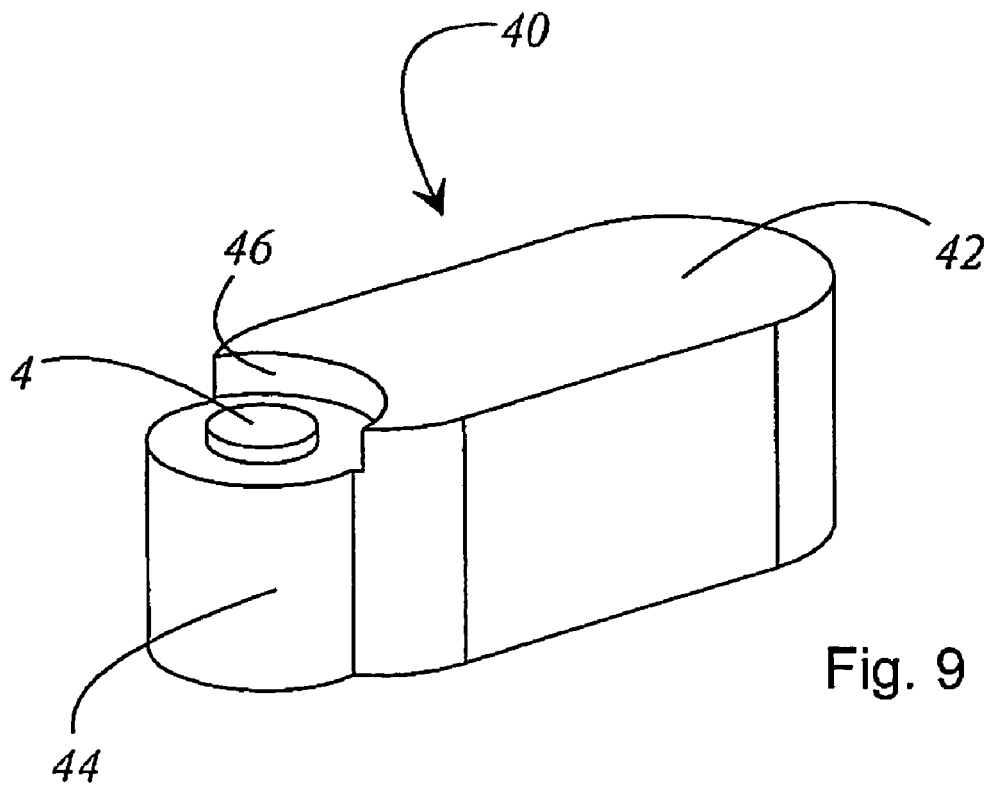
FIG. 9 is a perspective view of the polymerized embedding medium, ejected from the trough, that carries the specimen at one end.

FIG. 9 is a perspective view of polymerized body 40 made of embedding medium. Polymerized body 40 made of embedding medium is substantially a negative impression of trough 12 in trough plate 10 in which the embedding medium was polymerized. The polymerized body comprises an elongated oval part 42 that corresponds substantially to trough 12. Adjoining elongated oval part 42 is a round part 44 that corresponds to tapered portion 18 of trough 12. Round part 44 carries specimen 4. Step 46 configured in elongated part 42 has the shape of a circle sector. Step 46 is produced upon ejection of body 40 from trough 12. Ejection causes specimen carrier 2 to fall away from fully polymerized body 40. Specimen 4 thus remains behind on round part 44 of polymerized body 40.

What is claimed is:

1. An apparatus for cryosubstitution and embedding of biological specimens comprising: a container for receiving and holding at least one specimen carrier holding the specimen, wherein the container possesses the shape of a cylinder having a base and a sidewall and an opening opposite to the base, and a plurality of troughs are in the container, each trough being adapted for receiving a specimen carrier; wherein each of the troughs is configured with a tapering end and the tapered end of the troughs being arranged opposite the sidewall of the open cylinder, a step is provided in each trough against which a specimen carrier can rest and be held, said step being configured at the tapered end of each trough; and a supply conduit is provided for each of the troughs, so that a connection exists among the troughs.

2. The apparatus as defined in claim 1, wherein the supply conduits are connected to an introduction and extraction opening permitting an exchange of at least one medium through the supply conduits to the troughs.

3. The apparatus as defined in claim 2, wherein the introduction and extraction opening is connected to the supply conduits.

4. The apparatus as defined in claim 1, wherein the at least one trough, and the introduction and extraction opening, are configured in the interior of the cylinder; and the introduction and extraction opening possesses access to the at least one trough.

5. The apparatus as defined in claim 4, wherein the introduction and extraction opening is arranged centrally.

6. The apparatus as defined in claim 5, wherein the plurality of troughs are arranged radially around the introduction and extraction opening.

7. The apparatus as defined in claim 1, wherein the troughs are configured in a separate trough plate; and the trough plate is insertable into the container which has the conformation of an open cylinder.

8. The apparatus as defined in claim 7, wherein a UV-transparent annular film is placed onto the trough plate, the annular film being dimensioned such that an access to each trough still remains.

9. A method for cryosubstitution and embedding of biological specimens, comprising the following steps:
   placing at least one specimen carrier, carrying a specimen, into a container that encompasses multiple troughs each for receiving one specimen carrier;
   placing the specimen carrier against a step that is shaped into each of the troughs at a tapering end of the troughs;
   delivering and extracting at least one medium for cryosubstitution and embedding through an introduction and extraction opening; and that each of the troughs is equipped with a supply conduit so that a connection of the troughs to the introduction and extraction opening exists;
   polymerizing an embedding medium delivered to the troughs; and
   ejecting each shape present in the troughs, the polymerized shape carrying the specimen.

10. The method as defined in claim 9, wherein the specimen is arranged on an elevation of the polymerized shape; and the preparation carrier falls away upon ejection of the polymerized shape from the trough.

11. The method as defined in claim 9, wherein the container possesses the shape of a cylinder open at one end which comprises a base and a sidewall and is embodied with an opening opposite the base.

12. The method as defined in claim 11, wherein the at least one trough and the introduction and extraction opening are embodied in the interior of the cylinder; and the opening makes available access to the at least one trough and to the introduction and extraction opening.

13. The method as defined in claim 12, wherein the introduction/extraction opening is arranged centrally.

14. The method as defined in claim 11, wherein the multiple troughs are arranged radially around the introduction and extraction opening.

15. The method as defined in claim 9, wherein the tapered end of the troughs is arranged opposite the sidewall of the open cylinder.

16. The method as defined in claim 9, wherein the troughs are configured in a separate trough plate; and the trough plate is inserted into the container configured as an open cylinder.

17. The method as defined in claim 9, wherein when put in place, the specimen carrier is slid under the step; and the step partially wraps around the specimen carrier at the edge.

18. The method as defined in claim 9, wherein before polymerization of the embedding medium, a UV-transparent annular film is placed onto the trough plate, the annular film being dimensioned such that a partial access to each trough still remains.

19. The method as defined in claim 18, wherein the annular film is used as a cover for the trough plate; and as a result of coverage with the annular film, the embedding medium is polymerized uniformly and more rapidly.

20. The method as defined in claim 18, wherein a UV lamp is used for polymerization.

21. The method as defined in claim 9, wherein an ejection tool is used to remove the polymerized shape from the trough.

22. The method as defined in claim 9, wherein cryosubstitution, embedding, and polymerization are performed in a device for cryosubstitution.

23. A device for cryosubstitution comprising of an apparatus for cryosubstitution and embedding of biological specimens, wherein the apparatus defines a container for receiving at least one specimen carrier with a specimen, wherein the container possesses the shape of a cylinder having a base and a sidewall and an opening opposite to the base, a plurality of troughs are embodied in the container, each for receiving one specimen carrier; wherein each of the troughs is configured with a tapering end and the tapered end of the troughs being arranged opposite the sidewall of the open cylinder, a step against which the specimen carriers rest being configured at the tapered end of each trough; and a supply conduit is provided with each of the troughs, so that a connection exists among the troughs.

24. The apparatus as defined in claim 23, wherein the troughs are embodied in a separate trough plate; and the trough plate is inserted into the container configured as an open cylinder.

25. The apparatus as defined in claim 24, wherein the trough plate is embodied with introduction and extraction opening; and access to the at least one trough is made available through the introduction and extraction opening; and the introduction and extraction opening is arranged centrally.

* * * * *